(12) United States Patent
Lin

(10) Patent No.: US 7,701,650 B2
(45) Date of Patent: Apr. 20, 2010

(54) WIDE-ANGLE LENS MODULE AND ENDOSCOPE

(75) Inventor: Chun-Ling Lin, Taipei Hsien (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 31 days.

(21) Appl. No.: 12/108,021

(22) Filed: Apr. 23, 2008

(65) Prior Publication Data

US 2009/0052059 A1 Feb. 26, 2009

(30) Foreign Application Priority Data

Aug. 23, 2007 (CN) .................... 2007 1 0201441

(51) Int. Cl.
G02B 9/04 (2006.01)
G02B 9/64 (2006.01)
A61B 1/06 (2006.01)

(52) U.S. Cl. .................... 359/793; 359/755; 600/176

(58) Field of Classification Search ......... 359/749–756, 359/761–763, 770–771, 781–784, 793, 649–651, 359/656–657; 600/176; G02B 13/04
See application file for complete search history.

(56) References Cited

U.S. PATENT DOCUMENTS

| 5,754,345 | A | * | 5/1998 | Yamamoto | 359/754 |
| 6,956,703 | B2 | * | 10/2005 | Saito | 359/770 |
| 7,095,569 | B2 | | 8/2006 | Rege et al. | |
| 7,173,777 | B1 | * | 2/2007 | Lu et al. | 359/784 |
| 2007/0153386 | A1 | * | 7/2007 | Yamaguchi et al. | 359/557 |

FOREIGN PATENT DOCUMENTS

JP 05323183 A * 12/1993

* cited by examiner

Primary Examiner—Darryl J Collins
Assistant Examiner—Zachary Wilkes
(74) Attorney, Agent, or Firm—Andrew C. Cheng

(57) ABSTRACT

A wide-angle lens module includes a first lens and a second lens with negative refracting power, a third lens with positive refracting power, a fourth lens with negative refracting power, a fifth lens with positive refracting power, a sixth lens with positive refracting power, and a seventh lens with negative refracting power. The first lens, the second lens, the third lens, the fourth lens, the fifth lens, the sixth lens, and the seventh lens are disposed in order from an object side to an image side.

19 Claims, 8 Drawing Sheets

WIDE-ANGLE LENS MODULE AND ENDOSCOPE

BACKGROUND

1. Field of the Invention

The present invention generally relates to lens modules and endoscopes, and more particularly, relates to a wide-angle lens module and an endoscope using the wide-angle lens module.

2. Description of related art

In recent years, capsule type endoscopes have been widely used in the medical field. Generally, an endoscope includes a wide-angle lens module for capturing images of the body's internal organs such as the stomach, intestine and so on.

The viewing angle of the lens module is an important parameter when judging the performance of the lens module. However, the viewing angle of the lens module is relatively narrow, for example, a typical viewing angle is 110°.

What is desired is to provide a wide-angle lens module with a greater viewing angle and an endoscope using the wide-angle lens module.

SUMMARY

Accordingly, a wide-angle lens module is provided. The wide-angle lens module includes a first lens group with negative refracting power and a second lens group with positive refracting power. The first lens group and the second lens group are disposed in order from an object side to an image side. The first lens group and the second lens group satisfy: $-35<f_{12}/f<-10$, and $3.5<f_{14}/f<3.9$, wherein $f_{12}$ is an effective focal length of the first lens group, f14 is an effective focal length of the second lens group, f is a focal length of the wide-angle lens module. Moreover, an endoscope using the wide-angle lens module is provided.

Other advantages and novel features of the present invention will become more apparent from the following detailed description of an exemplary embodiment when taken in conjunction with the accompanying drawings.

DETAILED DESCRIPTION

Figure 1:
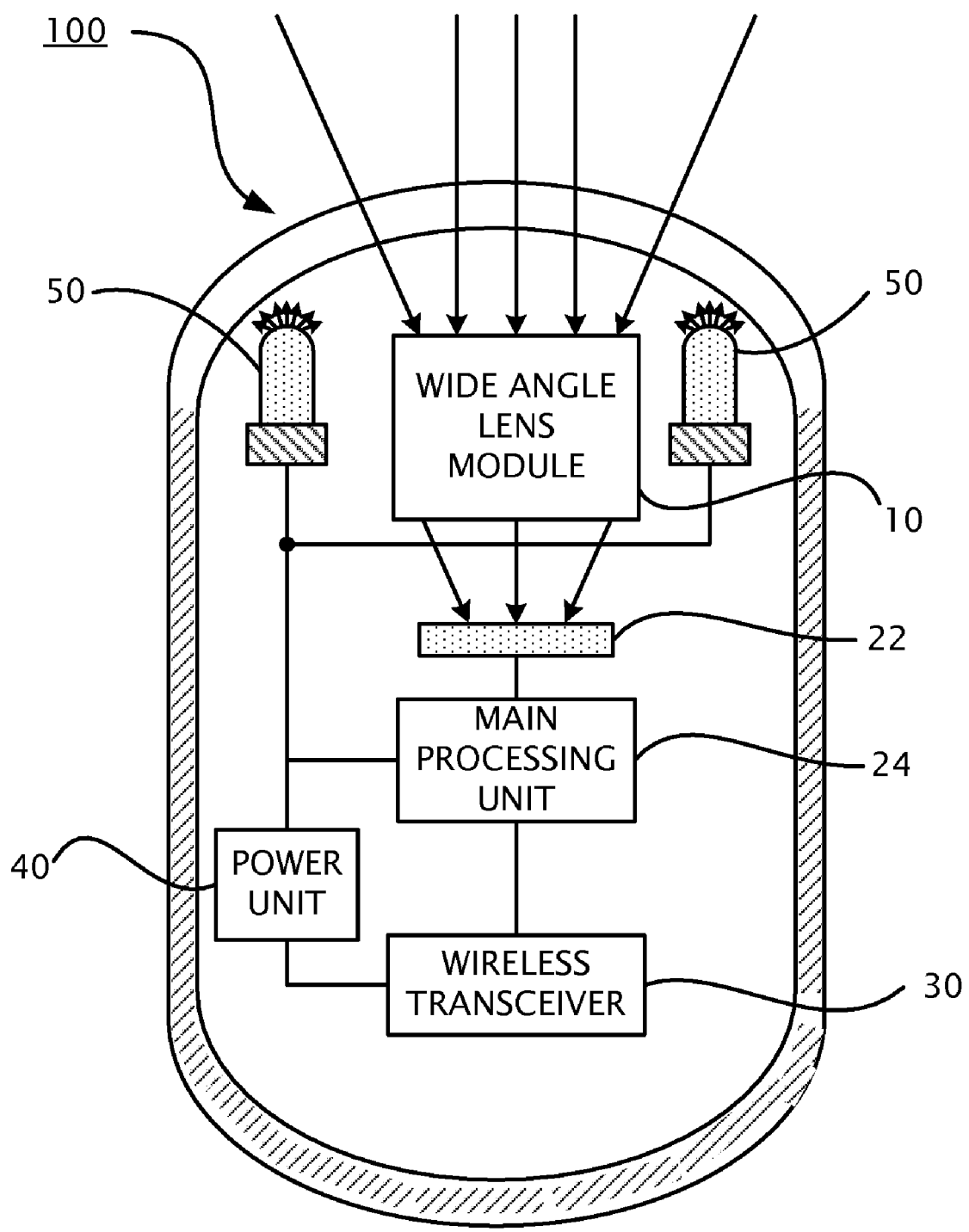
FIG. 1 is an endoscope having a wide-angle lens module according to an exemplary embodiment.

Referring to FIG. 1, an endoscope 100 is provided. The endoscope 100 includes a wide-angle lens module 10, an image sensor 22, a main processing unit 24, a wireless transceiver 30, a power unit 40, and a pair of lamps 50. The power unit 40 is electrically connected to the main processing unit 24, the wireless transceiver 30, and the lamps 50 for providing electrical power.

The lamps 50 are disposed at opposite sides of the endoscope 100. The lamps 50 emit light beams to illuminate a field of view. The wide-angle lens module 10 converges light beams reflected from objects in the field of view to the image sensor 22. The image sensor 22 converts the received light beams into electrical signals and transmits them to the main processing unit 24. The main processing unit 24 processes the electrical signals to get digital images. The digital images are encoded and transmitted by the wireless transceiver 30.

Figure 2:
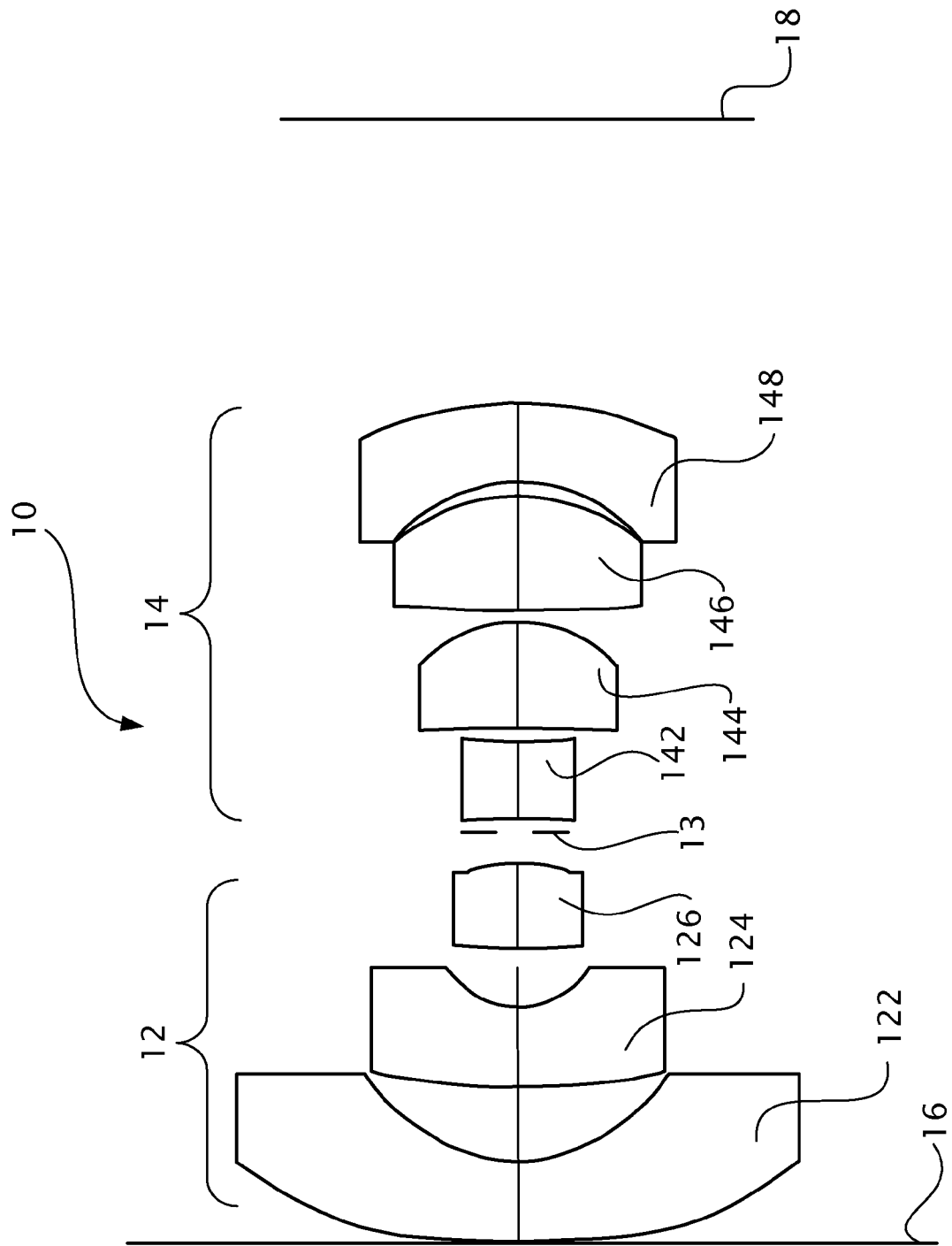
FIG. 2 is a cross sectional diagram of the wide-angle lens module shown in FIG. 1.

Referring to FIG. 2, the wide-angle lens module 10 includes a first lens group 12 and a second lens group 14. The first lens group 12 and the second lens group 14 are disposed in order from an object side 16 to an image side 18. The wide-angle lens module 10 is designed to be a fixed-focal type wide-angle lens module, i.e., a distance between the first lens group 12 and the second lens group 14 is not adjustable. Thus, the wide-angle lens module 10 can be miniaturized.

The first lens group 12 has negative refracting power for effectively receiving incident light beams at wide-angles. Preferably, the first lens group 12 satisfies the following condition: $-35<f_{12}/f<-10$ (1), wherein f is a system focal length of the wide-angle lens module 10, and $f_{12}$ is an effective focal length of the first lens group 12. The condition (1) is for configuring the wide-angle lens module 10 to have relatively smaller focal length so as to receive wide-angle light beams. If the ratio $f_{12}/f$ is below the lower limit −35, the viewing angle is less than 139°. If the ratio $f_{12}/f$ is above the upper limit 1.2, astigmatism becomes great and high-order spherical aberrations are difficult to correct.

The second lens group 14 has positive refracting power for converging light beams transmitted from the first lens group 12 to the image sensor 22. Preferably, the second lens group 14 satisfies the following condition: $3.5<f_{14}/f<3.9$ (2), wherein f is a system focal length of the wide-angle lens module 10, $f_{14}$ is an effective focal length of the second lens group 14. The condition (2) is for designing the wide-angle lens module 10 to be similar to a telecentric optical system, such that the light beams transmitted from the first lens group 12 may be more effectively converged to the image sensor 22. If the ratio $f_{14}/f$ is below the lower limit 3.5, coma aberration becomes great and lateral chromatic aberration is difficult to correct. If the ratio $f_{14}/f$ is above the upper limit 3.9, distortion becomes so great that it may be difficult to correct. The condition (2) is also used for balancing the refracting power of the wide-angle lens module 10 and limiting an overall length of the wide-angle lens module 10.

The first lens group 12 includes a first lens 122, a second lens 124, and a third lens 126 that are disposed in that order from the object side 16 to the image side 18. Both of the first lens 122 and the second lens 124 are meniscus lenses having negative refractive powers. Convex surfaces of the first lens 122 and the second lens 124 face toward the object side 16. Preferably, surfaces of the first lens 122 and the second lens 124 are aspheric for correcting spherical aberration. The shape of each aspheric surface is defined by the following expression:

$$x = \frac{cr^2}{1+\sqrt{1-(k+1)c^2r^2}} + \sum A_{2i}r^{2i}$$

wherein, x is a depth from the surface to a tangent plane of a vertex of the surface, r is a height from the optical axis of the system to the surface, c is a vertex curvature, k is a conic constant, and $A_{2i}$ are 2i-th order correction coefficients of the aspheric surface. The third lens 126 is a bi-convex lens having positive refractive power for further correcting the spherical aberration and the distortion.

The second lens group 14 includes a fourth lens 142, a fifth lens 144, a sixth lens 146, and a seventh lens 148. The fourth lens 142 is a spherical bi-concave lens having negative refracting power. The fifth lens 144 is a spherical meniscus lens having positive refracting power. A concave surface of the fifth lens 144 faces toward the image side 18. The sixth lens 146 is a spherical bi-convex lens having positive refracting power. The seventh lens 148 is a meniscus lens having negative refracting power. A convex surface of the seventh lens 148 faces toward the image side 18.

The first lens 122 satisfies the following condition: $-0.5 < D_1/f_{12} < -0.2$ (3), $n > 1.8$ (4), wherein $D_1$ is an effective light aperture of the first lens 122, $n_1$ is a refractive index of the first lens 122. The condition (3) is for configuring the first lens 122 to have a smaller light aperture. If the ratio $D_1/f_{12}$ is below the lower limit −0.5, the light aperture of the first lens 122 will be great. If the ratio $D_1/f_{12}$ is above the upper limit −0.2, the viewing angle of the wide-angle lens module 10 will be narrow. The condition (4) is for effectively increasing the incident angle of light beams to be received by the wide-angle lens module 10.

At least one of the fourth lens 142, the fifth lens 144, sixth lens 146, and seventh lens 148 satisfies the following condition: $v > 60$ (5), wherein v is an Abbe number of the fourth lens 142, the fifth lens 144, sixth lens 146, and seventh lens 148. The condition (5) is for effectively correcting the chromatic aberration of the wide-angle lens module 10.

Preferably, the wide-angle lens module 10 may further include an aperture stop 13. The aperture stop 13 is positioned between the third lens 126 of the first lens group 12 and the fourth lens 142 of the second lens group 14. The aperture stop 13 is used for providing an opening for restricting the amount of light beams transmitted from the first lens group 12 to the second lens group 14. That is, if the aperture stop 13 has a wider opening, the image brightness and definition may be increased, while the depth of field and contrast of the image are correspondingly decreased. It should be noted that, the aperture stop 13 may be positioned between other lens elements of the first lens group 12 or the second lens group 14 according to specific applications.

In order to control an overall length of the wide-angle lens module 10, the wide-angle lens module 10 preferably satisfies the following condition: $0.051 < f/TTL < 0.1$ (6), wherein TTL is an overall length of the wide-angle lens module 10. If the ratio f/TTL is below the lower limit 0.051, it is difficult to correct high-order spherical aberrations. If the ratio f/TTL is above the upper limit 0.1, it is difficult to effectively shorten the overall length of the wide-angle lens 10.

The following are symbols used in the exemplary embodiment.
  r: radius of curvature
  d: distance between adjacent two surfaces along optical axis of the wide-angle lens module 10
  n: refractive index of the lens at d-line
  v: Abbe number of the lens at d-line
  D: diameter of surface of the lens
  K: conic constant

EXAMPLE 1

Table 1 and table 2 shows lens data of the wide-angle lens module 10 of a first exemplary embodiment.

TABLE 1 f12/f = −15.331  f14/f = 3.711  D1/f12 = −0.4798  f/TTL = 0.067
n1 = 1.8601

| Surface | r(mm) | d(mm) | n | v | D(mm) |
|---|---|---|---|---|---|
| 1*st | 11.865 | 0.500 | 1.8061 | 40.4 | 3.5 |
| 2*nd | 0.748 | 0.477 | | | 1.880427 |
| 3*rd | 4.628 | 0.501 | 1.738019 | 45.3212 | 1.783733 |
| 4*th | 0.505 | 0.373 | | | 0.8622182 |
| 5th | 5.845 | 0.536 | 1.749704 | 27.8053 | 0.7655814 |
| 6th | −1.044 | 0.196 | | | 0.5785539 |
| 7th | Infinite | 0.080 | | | 0.2189654 |
| 8th | −2.975 | 0.500 | 1.755201 | 27.5795 | 0.3238109 |
| stop | 3.722 | 0.080 | | | 0.7164395 |
| 9th | −6.219 | 0.672 | 1.62041 | 60.3236 | 0.814093 |
| 10th | −0.858 | 0.080 | | | 1.249556 |
| 11th | 11.403 | 0.714 | 1.620411 | 60.3234 | 1.448011 |
| 12th | −1.226 | 0.091 | | | 1.559428 |
| 13th | −1.001 | 0.500 | 1.755199 | 27.5796 | 1.562495 |
| 14th | −2.336 | 1.800 | | | 2.000978 |

TABLE 2

| Surface | K | A4 | A6 | A8 | A10 |
|---|---|---|---|---|---|
| 1*st | 33.55368 | −0.019578 | −0.012724 | 0.0069822 | −0.006975 |
| 2*nd | −0.5111559 | −0.014654 | −0.011064 | 0.0064993 | −0.002921 |
| 3*rd | 0.01684907 | 0.058616 | 0.001572 | 0.000778 | 0.000902 |
| 4*th | −0.1337507 | 0.0135062 | −0.001376 | −0.000243 | −0.000234 |

Figure 3A:
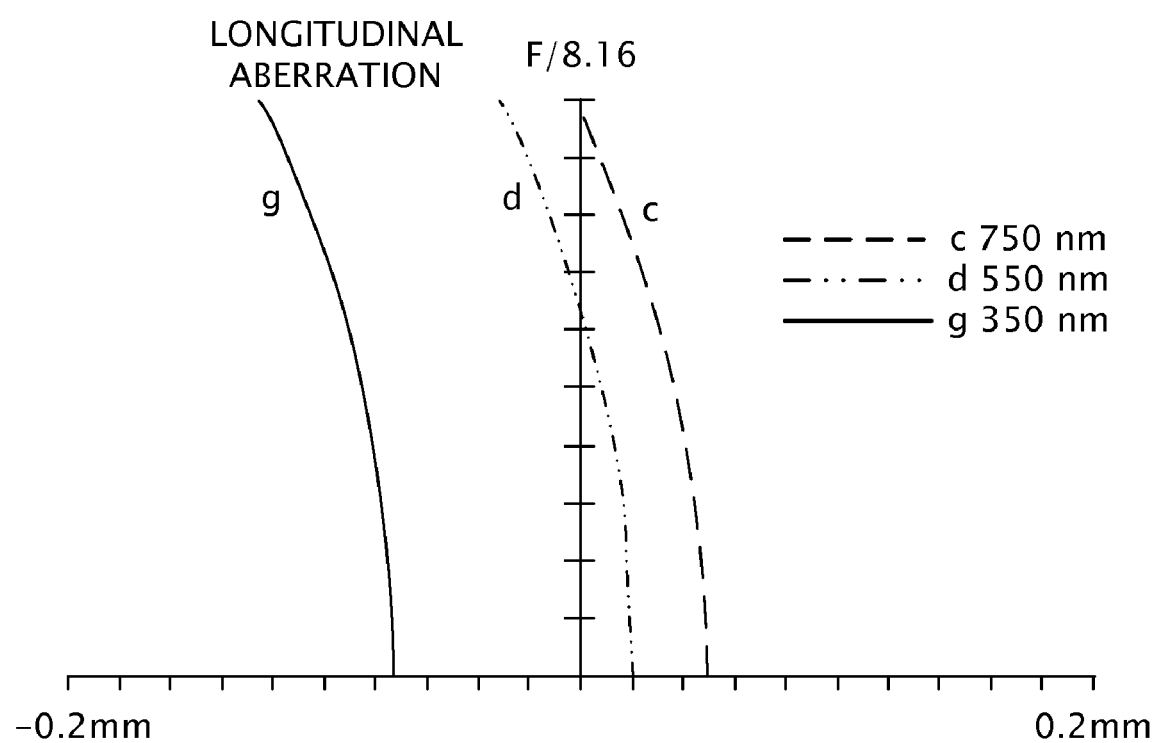
FIGS. 3A-3C respectively illustrate longitudinal spherical aberration, astigmatism, and distortion of the wide-angle lens module of a first exemplary embodiment.
Figure 3B:
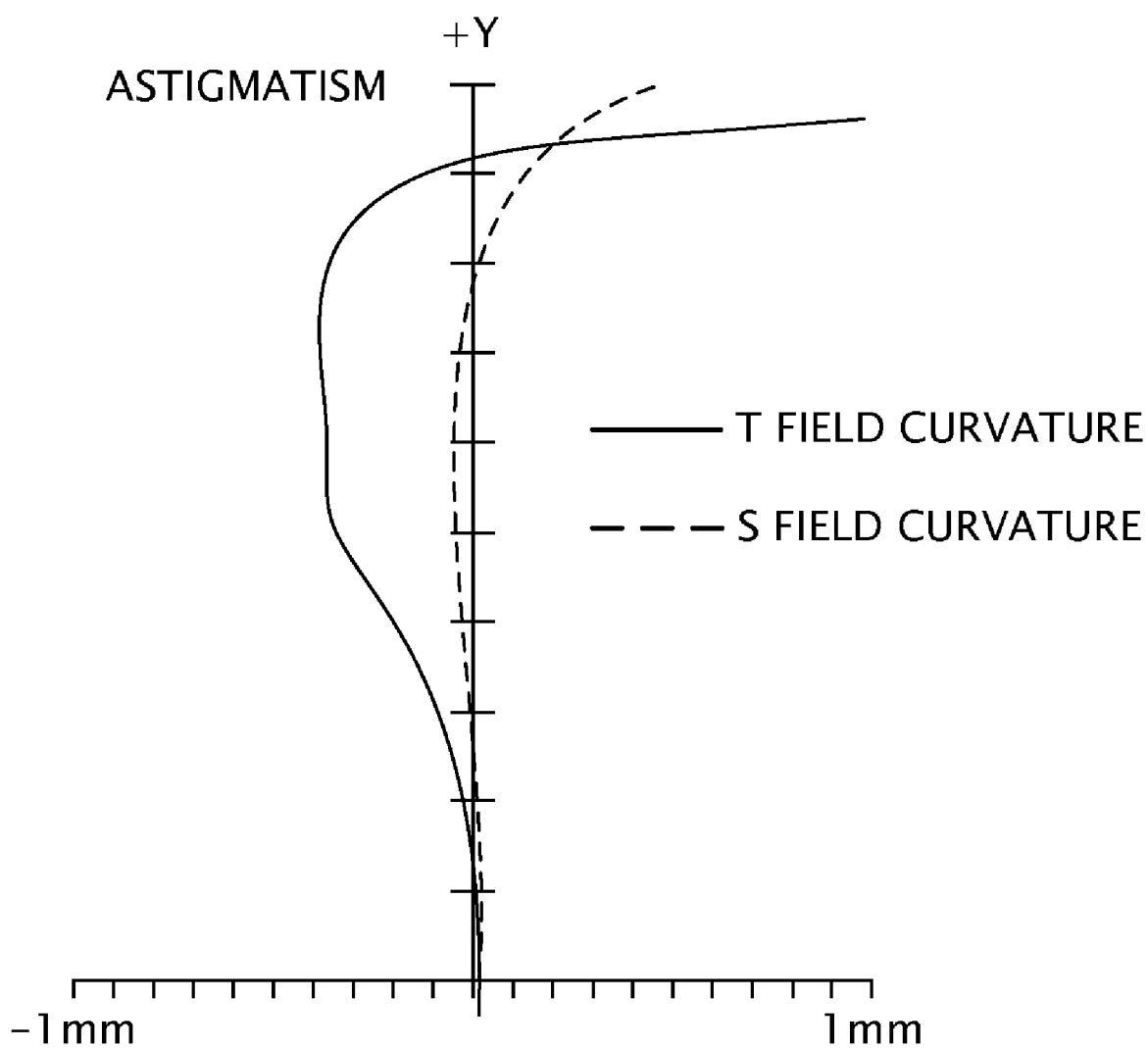
Figure 3C:
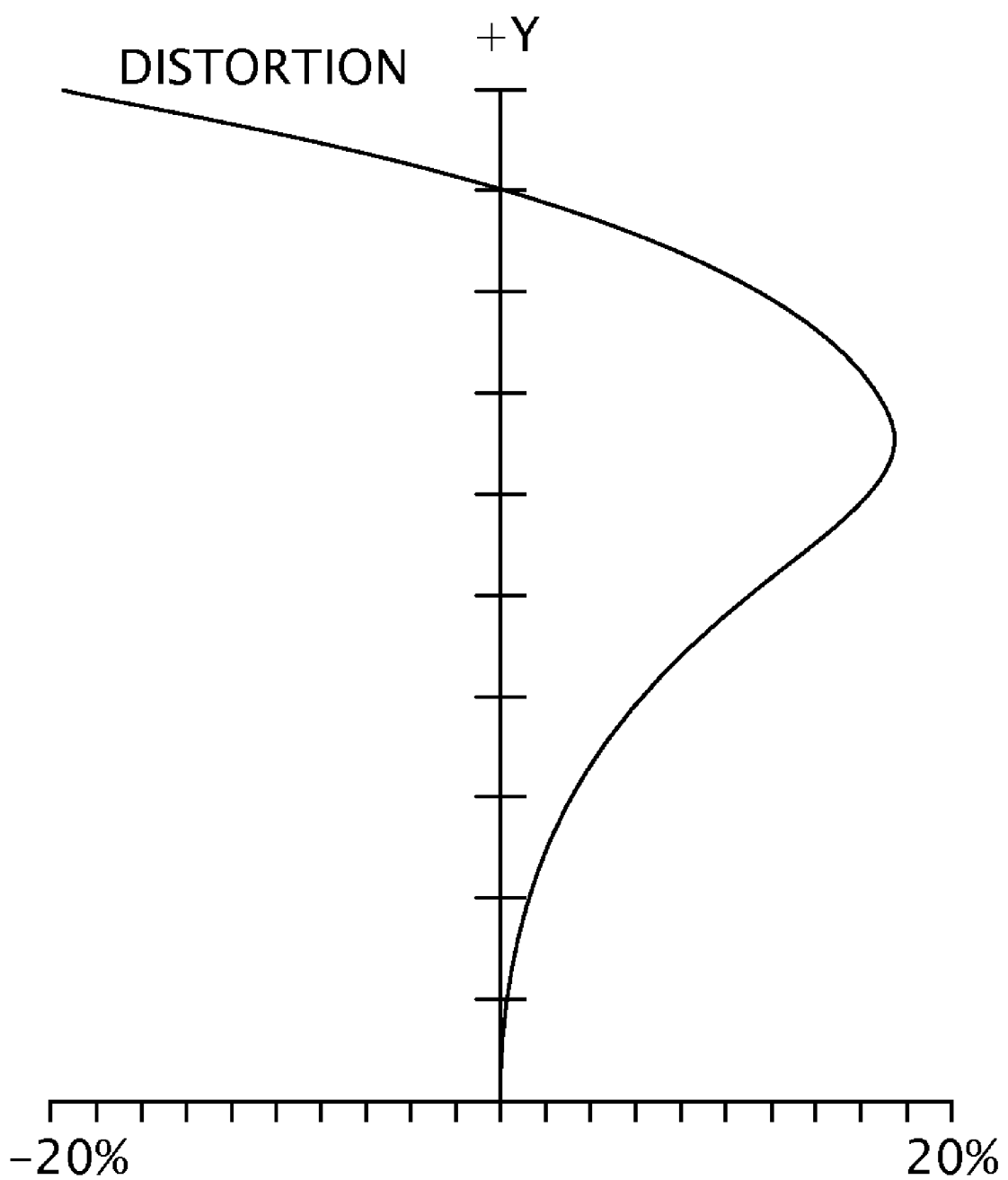

Referring to FIGS. 3A-3C, longitudinal spherical aberrations, astigmatism (field curvature), and distortion are respectively illustrated for the first embodiment of the wide-angle lens module 10 having lens data listed in table 1 and table 2, where viewing angle 2ω of the first embodiment can be as much as 149.2°.

EXAMPLE 2

Table 3 and table 4 show lens data of the wide-angle lens module 10 of a second exemplary embodiment.

TABLE 3 f12/f = −32.778  f14/f = 3.648  D1/f12 = −0.2072  f/TTL = 0.070
n1 = 1.8135

| Surface | r(mm) | d(mm) | n | v | D(mm) |
|---|---|---|---|---|---|
| 1*st | 11.615 | 0.520 | 1.8135 | 41.2 | 3.405146 |
| 2*nd | 0.743 | 0.442 | | | 1.813886 |
| 3*rd | 4.320 | 0.520 | 1.741629 | 45.0337 | 1.762527 |
| 4*th | 0.500 | 0.373 | | | 0.8543183 |
| 5th | 5.317 | 0.520 | 1.784696 | 26.2912 | 0.7627697 |
| 6th | −1.059 | 0.188 | | | 0.5918281 |
| 7th | infinite | 0.090 | | | 0.2276339 |
| 8th | −3.069 | 0.520 | 1.784696 | 26.2912 | 0.3361897 |
| stop | 3.716 | 0.090 | | | 0.7129198 |
| 9th | −7.259 | 0.662 | 1.62041 | 60.3236 | 0.823881 |
| 10th | −0.880 | 0.090 | | | 1.236191 |
| 11th | 10.007 | 0.696 | 1.620411 | 60.3233 | 1.417758 |
| 12th | −1.268 | 0.090 | | | 1.518855 |
| 13th | −1.025 | 0.520 | 1.755201 | 27.5795 | 1.513282 |
| 14th | −2.423 | 1.800 | | | 1.901408 |

TABLE 4

| Surface | K | A4 | A6 | A8 | A10 |
|---|---|---|---|---|---|
| $1^{*st}$ | 34.63731 | 0.054281572 | −0.004142308 | −0.000684573 | 0 |
| $2^{*nd}$ | −0.5097627 | −0.66751327 | 0.54314516 | 0.13826075 | −0.34252609 |
| $3^{*rd}$ | −0.5828592 | −0.000752106 | −0.000373065 | 0.000244308 | 0 |
| $4^{*th}$ | −0.1256545 | 0.35052806 | −0.87753926 | −13.147603 | 61.650754 |

Figure 4A:
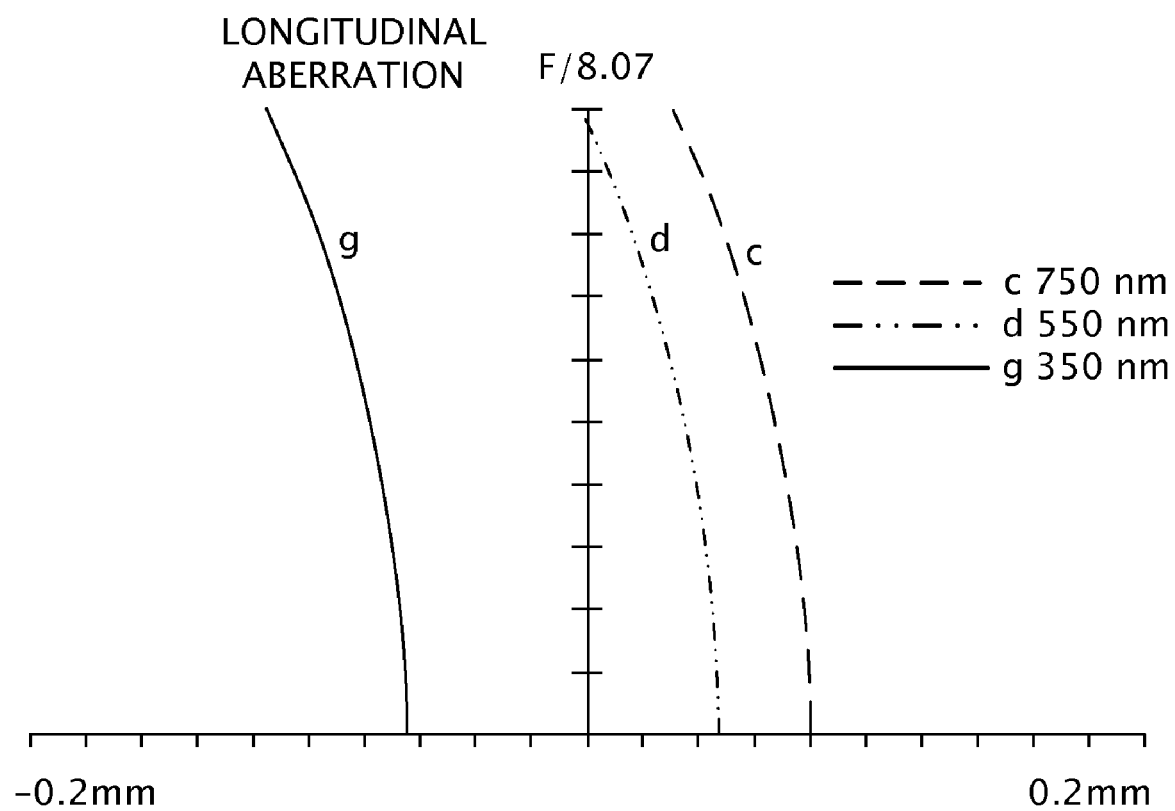
FIGS. 4A-4C respectively illustrate longitudinal spherical aberration, astigmatism, and distortion of the wide-angle lens module of a second exemplary embodiment.
Figure 4B:
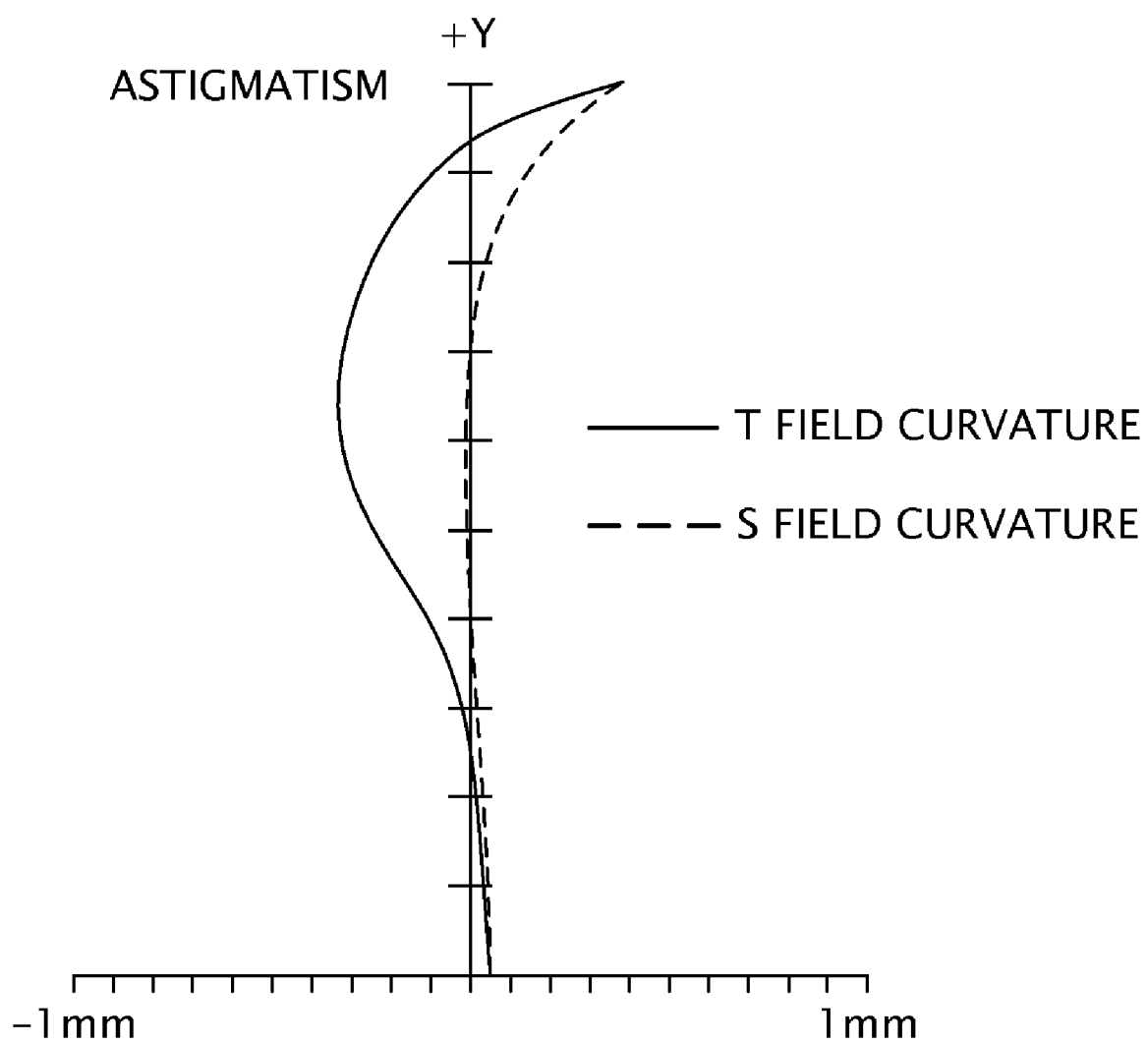
Figure 4C:
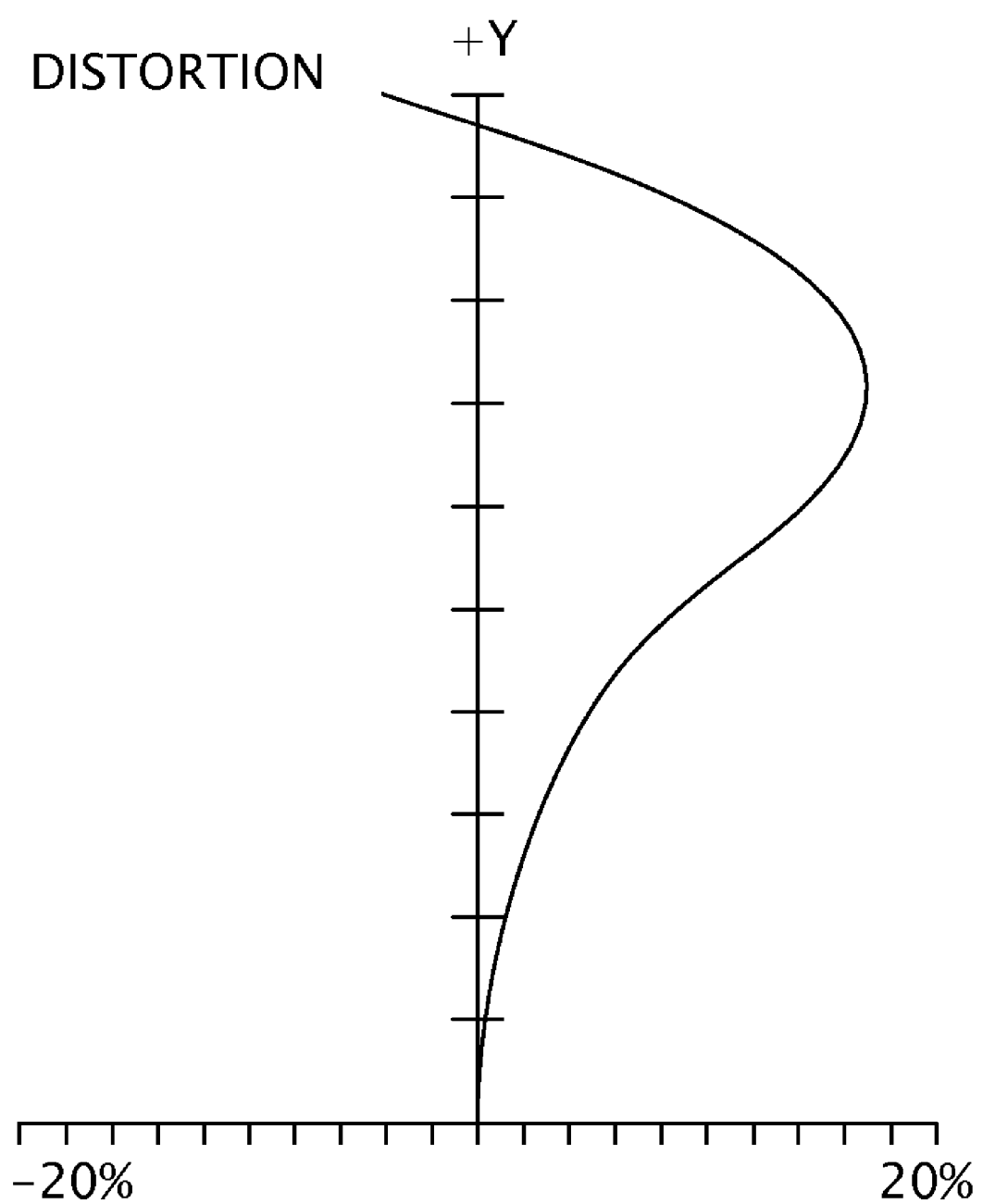

Referring to FIGS. 4A-4C, longitudinal spherical aberrations, astigmatism (field curvature), and distortion are respectively illustrated for a second example of the wide-angle lens module 10 having lens data listed in table 3 and table 4, where the viewing angle 2ω can be as much as 139.2°.

Alternative embodiments will become apparent to those skilled in the art to which the present invention pertains without departing from its spirit and scope.

What is claimed is:

1. A wide-angle lens module comprising:
   a first lens group with negative refracting power; and
   a second lens group with positive refracting power, the first lens group and the second lens group being disposed in order from an object side to an image side, the first lens group and the second lens group satisfying: $-35 < f_{12}/f < -10$, and $3.5 < f_{14}/f < 3.9$, wherein $f_{12}$ is an effective focal length of the first lens group, $f_{14}$ is an effective focal length of the second lens group, and f is a focal length of the wide-angle lens module.

2. The wide-angle lens module as described in claim 1, wherein the first lens group comprises:
   a first lens with negative refracting power, the first lens satisfying: $-0.5 < D_1/f_{12} < -0.2$, $n_1 > 1.8$, wherein $D_1$ is an effective light aperture of the first lens, and $n_1$ is a refractive index of the first lens;
   a second lens with negative refracting power; and
   a third lens with positive refracting power, the first lens, the second lens, and the third lens being disposed in order from the object side to the image side.

3. The wide-angle lens module as described in claim 2, wherein the first lens is a meniscus lens with at least an aspheric surface and has a convex surface facing toward the object side.

4. The wide-angle lens module as described in claim 2, wherein the second lens with at least an aspheric surface is a meniscus lens and has a convex surface facing toward the object side.

5. The wide-angle lens module as described in claim 2, wherein the third lens is a bi-convex lens.

6. The wide-angle lens module as described in claim 1, wherein the second lens group comprises:
   a fourth lens with negative refracting power;
   a fifth lens with positive refracting power;
   a sixth lens with positive refracting power; and
   a seventh lens with negative refracting power, the fourth lens, the fifth lens, the sixth lens, and the seventh lens being disposed in order from the object side to the image side, at least one of the fourth lens, the fifth lens, the sixth lens and the seventh lens satisfying: $v > 60$, wherein v is an Abbe number of the lenses.

7. The wide-angle lens module as described in claim 6, wherein the fourth lens and the sixth lens are bi-concave lenses, and the fifth lens is a meniscus lens.

8. The wide-angle lens module as described in claim 1, wherein the wide-angle lens module further satisfies: $2\omega > 139°$, wherein ω is a half viewing angle of the wide-angle lens module.

9. The wide-angle lens module as described in claim 1, wherein the wide-angle lens module further comprises:
   an aperture stop disposed between the first lens group and the second lens group.

10. An endoscope comprising:
    at least a lamp configured for emitting light beams to illumine a body's internal organ; and
    a wide-angle lens module for capturing images of the body's internal organ by receiving light beams reflected from the body's internal organ, the wide-angle lens module including:
    a first lens group with negative refracting power; and
    a second lens group with positive refracting power, the first lens group and the second lens group being disposed in order from an object side to an image side, the first lens group and the second lens group satisfying: $-35 < f_{12}/f < -10$, $3.5 < f_{14}/f < 3.9$, wherein $f_{12}$ is an effective focal length of the first lens group, $f_{14}$ is an effective focal length of the second lens group, and f is a focal length of the wide-angle lens module.

11. The endoscope as described in claim 10, wherein the lamp is located at lateral side of the wide-angle lens module.

12. The endoscope as described in claim 10, wherein the endoscope further comprises:
    a wireless transceiver configured for transmitting digital images captured from the wide-angle lens module.

13. The endoscope as described in claim 10, wherein the first lens group comprises:
    a first lens with negative refracting power, the first lens satisfying: $-0.5 < D_1/f_{12} < -0.2$, and $n_1 > 1.8$, wherein $D_1$ is an effective light aperture of the first lens, and $n_1$ is a refractive index of the first lens;
    a second lens with negative refracting power; and
    a third lens with positive refracting power, the first lens, the second lens, and the third lens being disposed in order from the object side to the image side.

14. The endoscope as described in claim 10, wherein the wide-angle lens module further satisfies: $2\omega < 139°$, wherein ω is a half viewing angle of the wide-angle lens module.

15. The endoscope as described in claim 10, wherein the second lens group comprises:
    a fourth lens with negative refracting power;
    a fifth lens with positive refracting power;
    a sixth lens with positive refracting power; and
    a seventh lens with negative refracting power, the fourth lens, the fifth lens, the sixth lens, and the seventh lens being disposed in order from the object side to the image side, at least one of the fourth lens, the fifth lens, the sixth lens and the seventh lens satisfying: $v > 60$, wherein v is an Abbe number of the fourth lens, the fifth lens, the sixth lens or the seventh lens.

16. The endoscope as described in claim 15, wherein the fourth lens and the sixth lens are bi-concave lenses, and the fifth lens is a meniscus lens.

17. A wide-angle lens module comprising:
    a first lens with negative refracting power;
    a second lens with negative refracting power;

a third lens with positive refracting power;
a fourth lens with negative refracting power;
a fifth lens with positive refracting power;
a sixth lens with positive refracting power; and
a seventh lens with negative refracting power, the first lens, the second lens, the third lens, the fourth lens, the fifth lens, the sixth lens, and the seventh lens being disposed in order from an object side to an image side of the wide-angle lens module wherein the wide-angle lens module satisfies: $-0.5 < D_1/f_{12} < -0.2$, and $n_1 > 1.8$, wherein $D_1$ is an effective light aperture of the first lens, $n_1$ is a refractive index of the first lens, and $f_{12}$ is an effective focal length of the first lens, the second lens and the third lens.

18. The wide-angle lens module as described in claim 17, wherein at least one of the fourth lens, the fifth lens, the sixth lens, and the seventh lens satisfies: $v > 60$, wherein $v$ is an Abbe number of the lenses.

19. The wide-angle lens module as described in claim 17, further satisfying: $2\omega > 139°$, wherein $\omega$ is a half viewing angle of the wide-angle lens module.

* * * * *